United States Patent [19]

Barr

[11] 4,317,796
[45] Mar. 2, 1982

[54] EXPLOSIVE GAS DETECTOR

[76] Inventor: Thomas A. Barr, 4618 Panorama Dr., Huntsville, Ala. 35801

[21] Appl. No.: 246,090

[22] Filed: Mar. 23, 1981

Related U.S. Application Data

[63] Continuation-in-part of Ser. No. 57,710, Jul. 16, 1979, Pat. No. 4,258,002.

[51] Int. Cl.³ .................. G01N 27/16; G01N 31/12
[52] U.S. Cl. .................................. 422/95; 422/98
[58] Field of Search ............... 23/232 E; 422/83, 94, 422/95, 96, 97, 98, 119

[56] References Cited

U.S. PATENT DOCUMENTS

| | | | |
|---|---|---|---|
| 2,219,540 | 10/1940 | Miller | 422/96 X |
| 2,782,102 | 2/1957 | Howe | 422/96 |
| 2,879,142 | 3/1959 | Jones et al. | 422/96 |
| 3,440,017 | 4/1969 | Palmer | 422/96 |
| 3,553,461 | 1/1971 | Siano et al. | 422/119 X |
| 3,574,553 | 4/1971 | Fertig | 422/96 |
| 3,907,503 | 9/1975 | Betts et al. | 422/67 |
| 4,258,002 | 3/1981 | Barr | 422/95 |

FOREIGN PATENT DOCUMENTS 269053  7/1970  U.S.S.R. .

Primary Examiner—Ronald Serwin
Attorney, Agent, or Firm—C. A. Phillips

[57] ABSTRACT

An explosive gas detector wherein power to a catalytic impedance element is held at a constant impedance level via a D.C., amplified, automatic bridge balancing circuit, and gas levels are indicated by an electrical meter connected between the output of a bridge and an adjustable level D.C. bias.

2 Claims, 1 Drawing Figure

EXPLOSIVE GAS DETECTOR

This application is a continuation-in-part of application bearing Ser. No. 57,710, entitled "Explosive Gas Detector", filed Jul. 16, 1979 now U.S. Pat. No. 4,258,002.

TECHNICAL FIELD

This invention relates generally to explosive gas detectors of the catalytic type, and particularly to a detector of this type wherein means are provided to limit temperature rise of the catalytic element.

BACKGROUND ART

It is known that explosive gas can be detected by an electrically heated wire having on it a catalytic material. Explosive gas causes a reaction with the catalytic material which produces additional heat, and this in turn changes the resistance of the wire. By metering the changes in resistance, as by the employment of an electrical bridge circuit, an indication of the concentration of gas is obtained.

There are several difficulties with this type of detector. A principal one is that the operation of the device depends on elevated temperatures of a catalytic element to provide indications, and the elevated temperatures in turn shorten the life of the element.

A second difficulty is that with use, the catalytic element changes character, and this requires recalibration of the detector.

A third difficulty is that at high levels of gas concentration, there is a tendency for the device to provide a lower than actual indication of gas, this occurring because of a thermal equilibrium which sometimes arises by virtue of a balance between reaction caused heating of the element and radiation given off by the element.

A fourth difficulty is that when operated at higher temperatures, the catalytic element has a tendency to fail in the presence of significant vibrations, and this is particularly a problem when a detector is used on or near mining machinery, as in a coal mine.

A fifth difficulty found in presently known gas analyzers of the catalytic type is that they have been relatively complex, employing alternating current systems of circuitry wherein power requirements both as to type and level made them basically incompatible for portable usage.

It is the object of this invention to overcome the above and other difficulties and to provide an improved explosive gas detector which is accurate, of simple structure, and anticipated to have a long operating life.

DISCLOSURE OF THE INVENTION

In accordance with this invention, an explosive gas detector would be constructed wherein power to a catalytic type sensor is controllably varied as a function of temperature reflected by its resistance, and the sensor is held at a relatively low temperature. The sensor is connected as an element in a direct current (D.C.), amplified, automatic balancing bridge circuit. A readily calibrated readout is provided by a voltage sensitive meter connected between the output of the bridge and a D.C. bias source through a potentiometer.

DETAILED DESCRIPTION OF THE DRAWING

Figure 1:
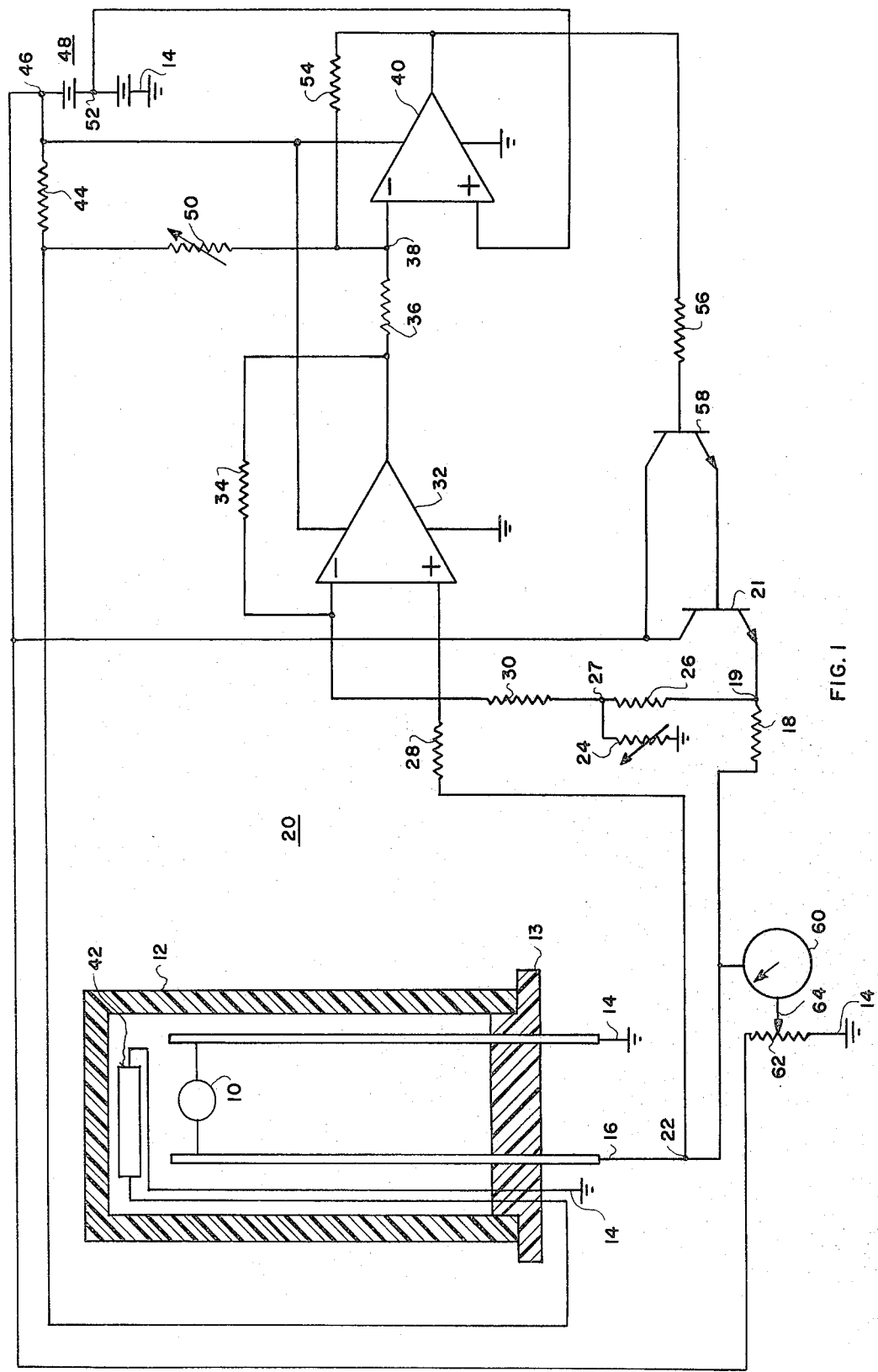
FIG. 1 is a schematic illustration of the structure and electrical system of the invention.

Referring to FIG. 1, a catalytic element 10 is employed as an explosive gas sensor. It is conventional, being formed of a resistance heating member (e.g., platinum wire) covered by a conventional coating containing palladium, which produces increased temperature in the presence of explosive gas. Catalytic element 10 is housed in a porour cover 12 on a base 13, which housing serves these purposes. First, if a spark should occur from the catalytic element, the spark would be contained. Second, the housing keeps air from being blown over the element, which might cause excessive cooling of it and interfere with accuracy; that is, while atmosphere may slowly enter through the pores of the wall of the housing, it may not enter with any significant velocity.

The heat state of catalytic element 10 is manifested by its resistance, its resistance varying with temperature, in turn produced by proportional level of explosive gas. The present invention contemplates operation on the positive characteristic portion of operation of element 10 where its resistance varies directly proportional to temperature. One terminal of element 10, terminal 14, is connected to ground, and the other terminal, terminal 16, is connected through a first bridge resistor 18 to the emitter terminal 19 of power transistor 21. This completes one side path of electrical bridge 20 to provide a signal output potential at terminal 22. A second side path of the bridge circuit exists between reference ground terminal 14 through variable resistor 24 and resistor 26 to the emitter terminal 19 of transistor 21. The output of bridge 20 appears at terminals 22 and 27, and it is connected through resistors 28 and 30 between the inverting and non-inverting inputs of amplifer 32. The output of amplifier 32 is connected to its negative, or inverting, input by feedback resistor 34 to effect a desired amplifier gain.

The output of amplifier 32 is connected through resistor 36 to a summing junction 38 connected to the negative input of operational amplifier 40. A second input is provided to summing junction 38 by a temperature compensation signal wherein thermistor 42, located within housing 12, is connected through load resistor 44 between +9 volts terminal 46 and ground of bias source 48. Changes in voltage across thermistor 42 are coupled through variable resistor 50 to summing junction 38.

A reference bias for amplifier 40 is provided by connecting the plus input terminal of the amplifier to the 4½ volts tap 52 of bias source 48. The gain of amplifier 40 is set at approximately 10 by feedback resistor 54 connected between the output and negative input of the amplifier.

Amplifier 46 drives, through resistor 56, the base input of PNP transistor 50, which is direct coupled through its emitter and collector to the basecollector terminals of PNP power transistor 21. The collectors of transistors 50 and 21, connected in cascade as emitter followers, are connected to the +9 volts terminal 46 of source 28. The emitter of transistor 21 is connected through catalytic element 10 to ground. Thus, transistor 21, via the signal flow just described, controls the current flow through catalytic element 10.

The output voltage across catalytic element 10 is compared with a selected reference voltage by voltage responsive, percent gas, meter 60. The reference voltage is provided by potentiometer 62 connected across bias source 48, an adjustable portion of this bias being supplied meter 60 via movable arm 64 of potentiometer 62.

To examine the operation of the system, assume that operating biases are applied to the circuit as shown, and as a result, catalytic element 10 is furnished a desired operating level of current. As described, the ultimate control voltage on transistor 54 will be derived from a voltage from D.C. bridge 20, and this output is initially adjusted in terms of the desired operating range for catalytic element 10 by adjustment of variable resistor 24, this being accomplished with no explosive gas present. Typically, this would be set at a minimum current level for resistance-temperature responsive operation of catalytic element 10. With variable resistor 24 at the selected level for this state, the signal between terminals 22 and 27 of bridge 20 will drive the signal loop through amplifiers 32 and 40 and transistors 58 and 21 to produce a current flow through the bridge, which will produce equal current flow through the combination of resistor 18 and impedance element 10 and the combination of resistor 26 and variable resistor 24 and thus produce a net zero potential across output terminals 22 and 27 of the bridge. At such level, percent gas meter 60 would be set by potentiometer 62 to provide a zero indication of percentage of gas present.

Assume next that the device is placed in an explosive gas environment and that the gas permeates through housing 12 and comes in contact with catalytic element 10. As a result, the element will increase its heat level, and this will be manifested in an increase in its resistance. As a result, the output of bridge 20, being positive going on the non-inverting (+) input of amplifier 32 with respect to its inverting input, would produce a positive going output of amplifier 32. This in turn will produce a negative going output of amplifier 40, and this output is applied through resistor 56 to the base input of transistor 58, causing it, a PNP transistor, to decrease its conduction. This effect is then fed by the emitter output of transistor 58 to the base input of power transistor 21 to cause its level of conduction to decrease, and thereby to decrease the voltage applied across terminals 16 and 19 and bridge 20. As a result, the voltage appearing across catalytic element 10 decreases, and this creates a relative increase in voltage (reference voltage minus voltage across catalytic element 10) across meter 16, which thus indicates an increased gas concentration present.

In order to provide an accurate readout of percentages of gas present, typically meter 60 would be calibrated prior to field use by the employment of calibrated samples of gas concentrations.

I claim:

1. An explosive gas detector comprising:
   a container having a gas entrance;
   a source of D.C. power having a ground reference terminal, and including a full voltage terminal and a fractional voltage terminal;
   impedance means positioned in said container, and having first and second terminals comprising;
   a conductor having the characteristic of an increase in resistance with an increase in temperature,
   a catalytic material coated on said conductor, which material increases in temperature in the presence of an explosive gas, and
   said first terminal being connected to said reference terminal of said power source;
   an electrical bridge comprising;
   said impedance,
   first and second resistors, each having first and second terminals,
   a variable resistor having first and second terminals,
   said first terminals of said first and second resistors being connected together as a bridge input terminal, said first terminals of said impedance element and variable resistor being coupled together to said ground reference terminal, and
   said second terminals of said first resistor and impedance means being connected together as a first output terminal, and said second terminals of said second resistor and variable resistor being connected together as a second output terminal;
   a transistor having its collector and emitter coupled in series between said full voltage terminal of said power source and said bridge input terminal and providing a power input to said bridge;
   first amplification means comprising an operational amplifier having its input coupled across said output terminals of said bridge;
   a container temperature responsive circuit comprising a thermistor positioned within said container, and a resistor connected in series with said thermistor between said reference terminal and one of said power terminals of said power source;
   a summing circuit comprising:
   a summing junction, and
   a first input to said summing junction comprising a resistor connected from the output of said operational amplifier;
   a second summing junction input comprising:
   a temperature responsive resistor in said container,
   a resistive load connected in series with said temperature responsive resistor and said source of D.C. power, and
   a variable resistor connecting the voltage across said temperature responsive resistor to said summing junction;
   a second operational amplifier, its inverting input being connected to said summing junction, and its non-inverting input being connected to said fractional voltage terminal of said power source;
   drive means connected to the output of said second operational amplifier for applying a drive signal to the base of said transistor for controlling the impedance of said transistor as a direct function of current flow through said impedance means, whereby the voltage applied to said impedance means is decreased as a function of explosive gas in said catalytic material; and
   indicating means responsive to voltage across said impedance means for indicating the quantity of gas present.

2. A detector as set forth in claim 1 wherein said indicating means comprises an electrical meter, a potentimeter having a pair of fixed terminals connected between said ground reference terminal of said power source and one of the other of said terminals of said power source and a movable terminal connected through said electrical meter to said second terminal of said temperature means.

* * * * *